United States Patent [19]

Howell et al.

[11] Patent Number: 5,177,006

[45] Date of Patent: Jan. 5, 1993

[54] ENZYMATIC RESOLUTION PROCESS

[75] Inventors: Jeffrey M. Howell, Chatham; Ramesh N. Patel, Bridgewater; Laszlo J. Szarka, East Brunswick, all of N.J.

[73] Assignee: E. R. Squibb & Sons, Inc., Princeton, N.J.

[21] Appl. No.: 724,643

[22] Filed: Jul. 2, 1991

Related U.S. Application Data

[63] Continuation-in-part of Ser. No. 427,078, Oct. 25, 1989, Pat. No. 5,128,263, which is a continuation-in-part of Ser. No. 219,624, Jul. 14, 1988, abandoned.

[51] Int. Cl.$^5$ ............................................. C12P 17/10
[52] U.S. Cl. ..................................... 435/121; 435/280
[58] Field of Search ............................... 435/280, 121

[56] References Cited

U.S. PATENT DOCUMENTS 4,629,701 12/1986 Sakimae et al. .

FOREIGN PATENT DOCUMENTS 0172614 2/1986 European Pat. Off. .
3740165 6/1988 Fed. Rep. of Germany .
8700517 9/1987 PCT Int'l Appl. .

*Primary Examiner*—Sam Rosen
*Attorney, Agent, or Firm*—Ellen K. Park

[57] ABSTRACT

A novel enzymatic resolution process for preparing resolved compounds of the formula

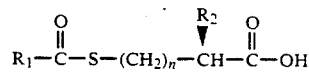

with improved yields and high optical purity is disclosed. Compounds of formula I' are useful, for example, as intermediates for the preparation of physiologically active compounds, e.g. captopril, zofenopril and endopeptidase inhibitor.

1 Claim, No Drawings

ENZYMATIC RESOLUTION PROCESS

This is a continuation-in-part of U.S. Ser. No. 427,078, filed Oct. 25, 1989, now U.S. Pat. No. 5,128,263, which is a continuation-in-part of U.S. Ser. No. 219,624 filed Jul. 14, 1988, now abandoned.

BACKGROUND OF THE INVENTION

Optically active carboxylic acids represented by the formula

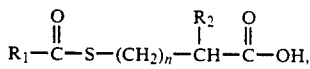

herein $R_1$ and $R_2$ are each independently selected from alkyl, cycloalkyl, aralkyl or aryl, and n is 1 or 2, are useful, for example, as intermediates for the synthesis of various physiologically active materials. For example, a compound of the formula

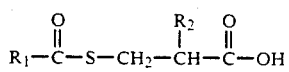

is a key intermediate in the synthesis of: 1-[(2S)-3-mercapto-2-methylpropionyl]-L-proline (captopril), having the formula

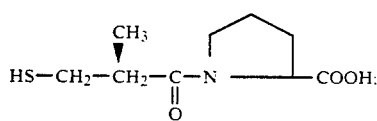

[1(R*),2α,4α]-1-[3-(benzoylthio)-2-methyl-1-oxopropyl]-4-(phenylthio)-L-proline (zofenopril), having the formula

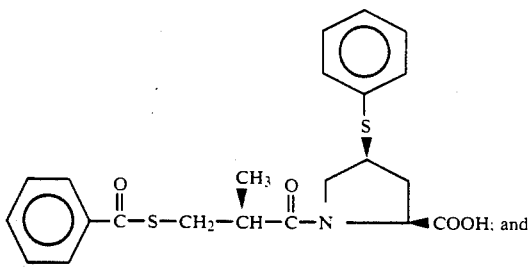

endopeptidase inhibitors having the formula

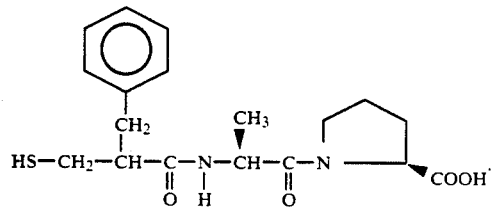

The beneficial activities of captopril, zofenopril and endopeptidase inhibitors of the above formula, depends on the configuration of the mercaptoalkanoyl moiety and the compound of the S configuration is about 100 times more potent than the corresponding R-enantiomer.

Prior art processes for making captopril have utilized chemical and enzymatic resolution procedures. For example, carboxylic acids of formula I are prepared as racemic mixtures which can be separated into the R and S-enantiomeric forms using chemical resolving agents. The so-provided S intermediates can then be used to prepare the desired product The chemical resolution techniques have the distinct disadvantage, however, that large amounts of very expensive resolving agents are required to make the desired enantiospecific products Additionally, the processes themselves are cumbersome and the yield is relatively low.

Alternatively, racemic compounds of the formula

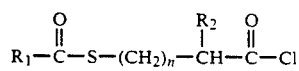

can be directly coupled to L-proline and derivatives thereof having the formula

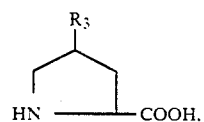

wherein $R_3$ is

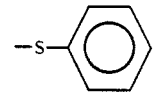

or —OH, and including salts and protected forms thereof, to produce diastereomers of the general formula

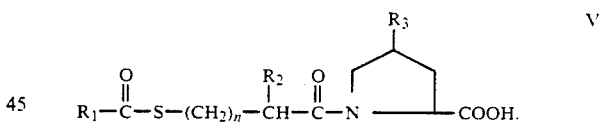

The SS-diastereomer of compound V can be isolated and thereafter reacted using known methodology to provide the desired resolved products. However, a drawback to this process is that an equal amount of the RS-diastereomer of compound V is formed which must be discarded. This is highly undesirable in view of the cost of the L-proline.

U.S. Pat. No. 4,629,701 provides the desired resolved form of the carboxylic acids of formula I by subjecting an ester of the formula

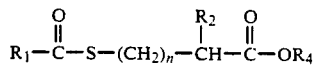

to an enzyme capable of asymmetrically hydrolyzing such an ester. It was found that while the

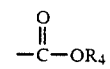

moiety is hydrolyzed to the acid form, the racemic ester is also resolved into the S or R configuration in improved yields and at lower costs than possible with chemical resolution techniques. However, there is still a considerable expense in making these ester starting materials and higher optical purity is still desired for more active products. Therefore, a process which is less expensive with improved yields and which provides enhanced optical purity would be a useful addition to the art.

BRIEF DESCRIPTION OF THE INVENTION

In accordance with the present invention, a novel process for preparing S-enantiomers of the formula

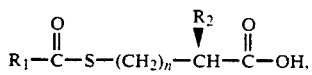
I' wherein $R_1$ and $R_2$ are each independently selected from alkyl, cycloalkyl, aralkyl or aryl, and n is 1 or 2, is provided The process comprises treating a racemic mixture of a compound of formula I with an enzyme or microorganism having the ability to stereoselectively hydrolyze the thioester bond of formula I, in the presence of a solvent.

The process also comprises the stereoselective esterification and hydrolysis of a racemic mixture of a compound of formula I with an enzyme or microorganism in the presence of a solvent.

DETAILED DESCRIPTION OF THE INVENTION

The following definitions apply throughout this application.

The term "alkyl" as used herein refers to substituted or unsubstituted straight or branched chain carbon groups of 1 to 20 carbon atoms, preferably 1 to 6 carbon atoms. Examples of suitable substituents include trifluoromethyl.

The term "cycloalkyl" as used herein refers to groups containing 5 to 7 carbon atoms.

The term "aryl" as used herein refers to monocyclic or bicyclic aromatic groups containing from 6 to 10 carbon atoms in the ring portion such as phenyl, naphthyl, and substituted phenyl or naphthyl containing substituents such as nitro, halogen, methyl or alkoxy groups on the aromatic ring.

The enzymatic resolution process of the present invention has the advantage that it can provide the desired S-enantiomers of formula I' with optical purity of 95 percent and above at yields exceeding 20 percent. Additionally, because the present process uses a racemic carboxylic acid of formula I as a starting material, instead of the carboxylic acid esters employed in prior art enzymatic processes, there is considerably less expense involved. These and other features make the process of the present invention very attractive for use in preparing optically active compounds of formula I', such as the S-enantiomer of the formula

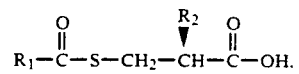
II' useful in the preparation of captopril, zofenopril and endopeptidase inhibitors described previously.

As discussed above, the prior art enzymatic processes function by the hydrolysis of the carboxy-ester, i.e. hydrolysis of the

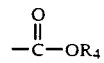

moiety in formula VI above to a

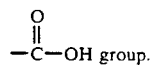 group.

In the present process, the racemic form of a compound of formula I is the starting material. Since this material does not include a carboxy ester, the enzyme or microorganism employed selectively catalyzes the hydrolysis of the thioester bond of one enantiomer of racemic I to yield the resolved form of the compounds of formula I' with high optical purity.

Methods for obtaining the racemic starting material of the formula

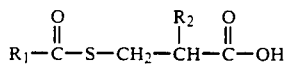
I are known.

For example, a compound of the formula

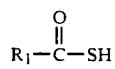
VII can be coupled to a compound of the formula

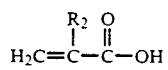
VIII in the presence or absence of a suitable solvent, such as hexane, heptane or isopropanol, under the usual conditions for conducting such an addition reaction.

The present process can be carried out in an aqueous solvent, or organic solvent or mixtures thereof. Typical solvents suitable for use in the present process include, but are not limited to, 1,1,2-trichloro-1,2,2-trifluoroethane, toluene, cyclohexane, benzene, deionized water, suitable aqueous buffer solutions and mixtures of these organic and aqueous solvents.

The enzyme or microorganism used in the present process can be any enzyme or microorganism having the ability to stereoselectively hydrolyze thioesters of the general formula I. The process also comprises the use of enzymes or microorganisms having the ability to stereoselectively esterify the carboxyl group and hydrolyze thioesters of the racemic compounds of the general formula I. Various enzymes, such as esterases, lipases and proteases regardless of origin or purity, are suitable for use in the present invention. The enzyme can be in the form of a mixture of animal and plant enzyme, cells of microorganisms, crushed cells or extracts of cells.

Typical genuses of microorganisms suitable as sources of hydrolyzing enzymes include Mucor, Escherichia, Staphylococcus, Agrobacterium, Rhizopus, Aspergillus, Nocardia, Streptomyces, Trichoderma, Candida, Rhodotorula, Torulopsis, Bacillus, Alcaligene, Pseudomonas, Brevebacterium, Enterobacter, Chromobacterium, Arthrobacter, Microbacterium, Mycobacterium, Saccharomyces, Penicillium, Botrytis, Chaetomium, Ophiobolus, Cladosporium, Candida, Geotrichum and the like.

Commercially available enzymes suitable for use in the present invention include lipases, such as Amano AY-30 (*Candida cylindracea*), Amano P (*Pseudomonas fluorescens*), Amano N (*Rhizopus niveus*), Amano R (*Penicillium sp.*), Amano FAP (*Rhizopus oryzae*), Amano AP-12 (*Aspergillus niger*), Amano MAP (*Mucor meihei*), Amano GC-4 (*Geotrichum candidum*), Sigma L-0382 (porcine pancreas), Sigma L-3001 (Wheat germ), Sigma L-1754 (*Candida cylindracea*), Sigma L-0763 (*Chromobacterium viscosum*), and Amano K-30 (*Aspergillus niger*), Novo Lipolase, Pseudomonas lipase from Biocatalysts, and Pseudomonas lipase from Enzymatics. Additionally, enzymes derived from animal tissue include esterase from pig liver, α-chymotrypsin and pancreatin from pancreas.

Specific microorganisms suitable for use in the present process include *Pseudomonas fluorescens, Pseudomonas putida, Pseudomonas ovalis, Escherichia coli, Staphylococcus aureus, Geotrichum candidum, Alcaligenes faecalis, Steptomyces griseus, Streptomyces clavuligerus, Nocardia erthropolis, Nocardia asteraides, Mycobacterium phlei, Agrobacterium radiobacter, Aspergillus niger, Rhizopus oryzae* and the like.

To carry out the process of the present invention, the enzyme and racemic starting material are added to the desired solvent. Typically, the enzyme is adsorbed onto a suitable carrier, e.g. diatomaceous earth (porous Celite Hyflo Supercel), or the like. This serves the purpose of immobilizing the enzyme which has the effects of controlling the enzyme particle size and preventing aggregation of the enzyme particles when used in an organic solvent. This can be accomplished, for example, by precipitating an aqueous solution of the enzyme with cold acetone in the presence of the Celite Hyflo Supercel followed by vacuum drying. The reaction solution typically contains between about 5 and 200 mg of racemic starting material per ml of solvent, and preferably contains about 15-50 mg/ml. The enzyme added to the reaction solution may be present in concentrations ranging from about 5 to about 40 mg of enzyme per ml of solvent. While it is desirable to use the least amount of enzyme possible, the amount of enzyme required will vary depending upon the specific activity of the enzyme used.

When the reaction is conducted in an organic solvent, small amounts of water may be added to the reaction mixture. The water added to the reaction mixture may be present in concentrations ranging from about 0.2 to about 100 mg of water per ml of solvent, or solvent saturated with water, and preferably is present in an amount of about 0.8-5 mg/ml. When an aqueous buffer solution or deionized water is used as the solvent for the reaction, the pH of the reaction solution may be between about 3 and 10, and is preferably maintained at about 5-8 by the addition of suitable materials. Incubation of the reaction solution can be at a temperature between about 4° and about 60° C. and is preferably carried out at about 30° C. The reaction time can be appropriately varied depending upon the amount of enzyme used and its specific activity. Typical reaction times for optical purities of 90 percent and above are at least about 5 hour and can range up to about 50 hours for greater conversions and higher optical purities, e.g. optical purities exceeding 95 percent. Optically active I′ can be isolated from the reaction mixture and purified by known methodologies such as extraction, distillation, crystallization, column chromatography, and the like.

As will be apparent to those skilled in the art, the process of the present invention can be carried out using microbial cells containing an enzyme having the ability to stereoselectively hydrolyze thioesters of racemic compounds of the general formula I. Additionally, the process of the present invention can be carried out using microbial cells containing an enzyme having the ability to stereoselectively esterify carboxyl groups as well as hydrolyze thioesters of racemic compounds of the general formula I. When using a microorganism to perform the resolution, the present process is conveniently carried out by adding the cells and the racemic starting material to the desired solvent. Cells may be used in the form of intact cells, dried cells such as lyophilized, spray-dried or heat-dried cells, immobilized cells, or cells treated with organic solvents such as acetone or toluene. Cells may also be used in the form of treated cell material such as ruptured cells or cell extract.

Using the methodology of U.S. Pat. No. 4,105,776, the resolved acid of formula I′ or its chemical equivalent is used to acylate L-proline having the formula

forming captopril, i.e. the compound of formula III. The thioester formed by the coupling of compound I with compound IX can be deacylated by conventional means, such as by ammonolysis (e.g., by treatment with alcoholic ammonia or concentrated ammonium hydroxide) or by alkaline hydrolysis (e.g., by treatment with aqueous metal hydroxide). Alternatively, again employing methodology from U.S. Pat. No. 4,105,776, the resolved acid of formula I′ can be used by removing the acetyl group (by conventional methods) and thereafter dehydrating the so-treated acid to form a thiolactone of the formula

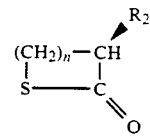

The thiolactone X can thereafter be used to acylate the L-proline of formula IX to obtain the desired product.

Similarly, to provide zofenopril, i.e., the compound of the formula

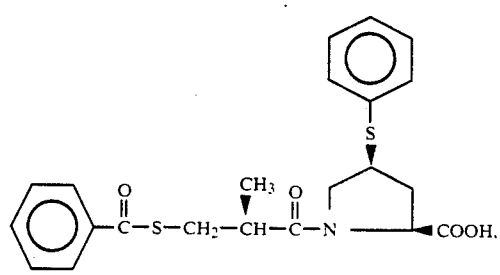

the resolved acid of formula I' or its chemical equivalent where $R_1$ is

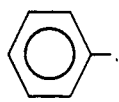

is used to acylate a compound of the formula

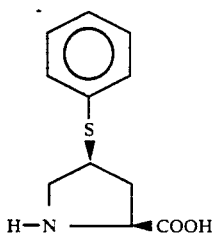
XII as described in U.S. Pat. No. 4,316,906. Alternatively, using the methodology of U.S. Pat. No. 4,316,906, the compound of formula I' where $R_1$ is

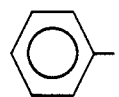

can be coupled with a compound of the formula

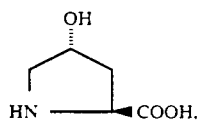
XIII or eaters or protected forms thereof, to provide a compound of the formula

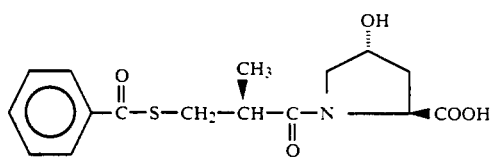
XIV which can thereafter be treated with a compound of the formula

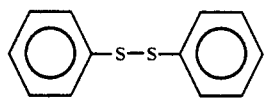
XV or

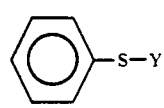
XVI where Y is an activating group such as succinimide or phthalamido or a halide such as Cl or Br to provide the product of formula IIIa.

The acylation of compounds IX or XII with the resolved acid of formula I' can be effected in the presence of a coupling agent like dicyclohexycarbodiimide or the like, or the acid can be activated by formation of its mixed anhydride, symmetrical anhydride, acid chloride, acid ester or use of Woodward reagent K, N-ethoxycarbonyl-2-ethoxy-1,2-dihydroquinoline or the like. For a review of the methods for acylation, see *Methoden der Organischen Chemie* (Houben-Weyl), Vol. XV, part II, page 1 et seq. (1974).

Compounds of formula IIIb may be prepared by alkylating the resolved acid of formula I' with the ala-proline benzyl ester tosic acid having the formula

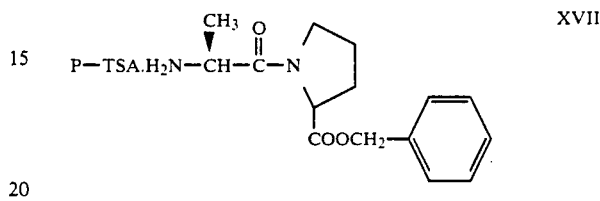
XVII to form a compound of the formula

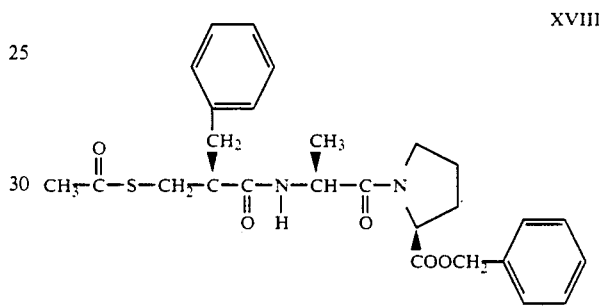
XVIII

Compounds of formula XVIII are saponified to form compounds of formula IIIb.

Compounds of formula XVII may be prepared by coupling Boc-alanine with the proline benzyl ester hydrochloride salt to form a Boc protected alanine proline benzyl ester having the formula

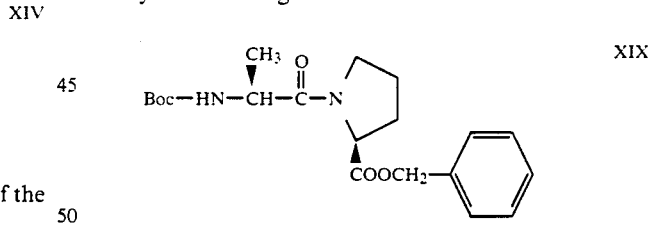
XIX

Compounds of formula XIX are then reacted with trifluoroacetic acid to remove the Boc group, then reacted with tosic acid to produce the tosic salt having the formula XVII.

The present invention will now be described by the following examples, however, it should be understood that the invention is not meant to be limited by the details therein.

EXAMPLE 1

To a solution of racemic 3-acetylthio-2-methylpropanoic acid (405 mg) in 25 ml of 1,1,2-trichloro-1,2,2-trifluorethane (CFC-113) was added 1.0 g of lipase from *Pseudomonas fluorescens* (Amano lipase P-30) and 90 mg of deionized water. The reaction mixture was shaken on a gyrotary shaker at 280 rpm at 30° C. The degree of conversion was followed by gas chromatography of reaction mixture filtrates. After 16 hours, the conversion was 84% based on the racemic material initially present. The enantiomeric composition of the remaining unreacted substrate (obtained in 16% reaction yield) was 97.8% S-enantiomer and 2.2% R-enantiomer of 3-acetylthio-2-methylpropanoic acid (enantiomeric excess=95.6%). In this and all following examples, the enantiomeric composition of the unreacted 3-acetylthio-2-methylpropanoic acid fraction was determined by capillary gas chromatography following derivatization with thionyl chloride and esterification of the resulting acid chloride with (S)-(+)-2-octanol to form diastereomeric esters which can be separated by capillary GC.

EXAMPLE 2

10.0 g of lipase from *Pseudomonas fluorescens* (Amano lipase P-30) was added to 50 ml deionized water and the mixture centrifuged for 10 minutes at 1,000×G. A 40 ml portion of the supernatant was diluted to 200 ml with deionized water and to this enzyme solution was added 40 g of Celite Hyflo Supercel (diatomaceous earth supplied by Manville Corporation). The mixture was incubated for 3 hours at 28° C. with gentle stirring. The enzyme was then precipitated onto the Hyflo Supercel by slowly adding 300 ml of ice-cold acetone to the mixture while stirring. The mixture was filtered on a sintered glass vacuum filter and the filter cake washed with 300 ml ice-cold acetone. The preparation was dried in a vacuum evaporator at 50° C. for 18 hours to yield an immobilized enzyme preparation with a water content of 0.45% w/w (Karl Fischer moisture analysis).

A 2 g portion of the above immobilized enzyme preparation was added to a solution of racemic 3-acetylthio-2-methylpropanoic acid (405 mg) in 25 ml of 1,1,2-trichloro-1,2,2-trifluorethane (CFC-113). To this mixture, 60 mg of deionized water was added and the reaction mixture shaken on a gyrotary shaker at 280 rpm at 30° C. The degree of conversion was followed by high-pressure liquid chromatography (HPLC) of reaction mixture filtrates. After 12 hours, the conversion was 78% based on the racemic substrate initially present. The enantiomeric composition of the remaining unreacted substrate (obtained in 22% reaction yield) was 97.1% S-enantiomer and 2.9% R-enantiomer of 3-acetylthio-2-methylpropanoic acid (enantiomeric excess=94.2%) as determined by capillary gas chromatography following derivatization.

EXAMPLE 3

A 2 g portion of the immobilized enzyme preparation described in Example 2 was added to a solution of racemic 3-acetylthio-2-methylpropanoic acid (405 mg) in 25 ml of toluene. To this mixture, 60 mg of deionized water was added and the reaction mixture shaken on a gyrotary shaker at 280 rpm at 28° C. After 28 hours, the conversion was 79% complete (HPLC analysis) based on the racemic substrate initially present. The enantiomeric composition of the remaining unreacted substrate (obtained in 21% reaction yield) was 97.5% S-enantiomer and 2.5% R-enantiomer of 3-acetylthio-2-methylpropanoic acid (enantiomeric excess=95.0%).

EXAMPLE 4

405 mg of racemic 3-acetylthio-2-methylpropanoic acid was dissolved in 15 ml of deionized water, the pH adjusted to 5.0 with 1 N sodium hydroxide, and the solution diluted to 25 ml with deionized water. This solution was placed in a magnetically stirred pH-stat vessel at 40° C. with pH maintained at 5.0 by the addition of 0.5 N sodium hydroxide. To this solution was added 1.0 g of lipase from *pseudomonas fluorescens* (Amano lipase P-30) and the degree of conversion followed by HPLC analysis. After 40 hours, the conversion was 76% based on the racemic substrate initially present. The enantiomeric composition of the remaining unreacted substrate (obtained in 24% reaction yield) was 85.7% S-enantiomer and 14.3% R-enantiomer of 3-acetylthio-2-methylpropanoic acid (enantiomeric excess=71.4%) as determined by capillary gas chromatography following derivatization.

EXAMPLE 5

To a solution of racemic 3-acetylthio-2-methylpropanoic acid (405 mg) in 25 ml of 1,1,2-trichloro-1,2,2-trifluoroethane (CFC-113) was added 1.05 g of dried mycelia of *Rhizopus oryzae* (ATCC 24563) and 75 mg of deionized water. The reaction mixture was shaken on a gyrotary shaker at 280 rpm at 28° C. After 69 hours, the conversion was 73% complete (HPLC analysis) based on the racemic substrate initially present. The enantiomeric composition of the remaining unreacted substrate (obtained in 27% reaction yield) was 95.9% S-enantiomer and 4.1% R-enantiomer of 3-acetylthio-2-methylpropanoic acid (enantiomeric excess=91.8%).

EXAMPLE 6

To a solution of racemic α-[(Acetylthio) methyl]benzenepropanoic acid (250 mg) in 10 mL of toluene was added 1 g of lipase from *Pseudomonas fluorescens* (Amano lipase P-30) and 0.1% (w/v) water. The reaction mixture was shaken on a gyrotary shaker at 280 rpm at 30° C. The degree of conversion was followed by gas chromatography of reaction mixture filtrates. After 16 hours, the conversion was 60% based on the racemic material initially present. The enantiomeric composition of the remaining unreacted substrate (obtained in 40% reaction yield) was 98.0% S-enantiomer and 2.0% R-enantiomer of α-[(Acetylthio)methyl]benzenepropanoic acid, (enantiomeric excess = 96.0%).

In this and all following examples the enantiomeric composition of α-[(Acetylthio)methyl]]benzenepropanoic acid was determined by chiral HPLC system.

Lipase P-30 from *Pseudomonas fluorescens* catalyzed the hydrolysis of the thioester bond of formula I. Mainly the undesired enantiomer of racemic compound I was hydrolyzed leaving the desired enantiomer enriched during the reaction. The reaction is represented as follows:

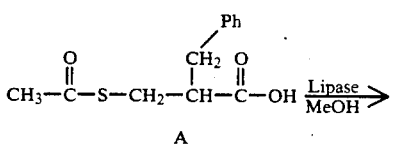

A

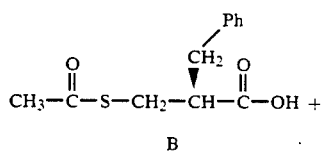

B

-continued

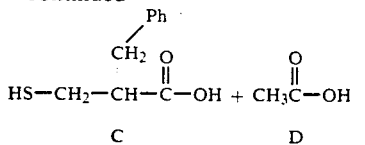

The reaction was monitored by gas chromatography at 130° C. injector temperature, 250° C. detector temperature (flame ionization detector) and oven temperature of gradient of 130° C. to 220° C. at rate of 10° C./minute. Under the above conditions the retention times for compound A and B is 8.28 minutes, compound C is 5.95 minutes.

The optical purity of compound B was determined by chiral HPLC system using chiralcel AGP column (100 mm×4 mm, 5 μm particle size) under the following conditions:

| Mobile Phase: | 89% 0.005M potassium phosphate, monobasic pH 4.75 11% acetonitrile |
|---|---|
| Flow Rate: | 0.7 mL/min |
| Temperature: | 25° C. |
| Injection volumn: | <5 μl |
| UV detection: | 245 nm |

The retention time for the R-enantiomer of the racemic compound A was 9.095 minutes and for the S-enantiomer was 14.910 minutes.

EXAMPLE 7

Same as example 6, except, Pseudomonas lipase from Biocatalyst Co. was used as the enzyme source. After 40 hours, the conversion was 80% based on the racemic material initially present. The enantiomeric composition of the remaining unreacted substrate (obtained in 20% reaction yield) was 97% S-enantiomer and 2% R-enantiomer of α-[(Acetylthio)methyl]benzenepropanoic acid (enantiomeric excess=95%).

EXAMPLE 8

Same as example 6, except, Pseudomonas lipase from Eneymatics Co. was used as the enzyme source. After 40 hours, the conversion was 78% based on the racemic material initially present. The enantiomeric composition of the remaining unreacted substrate (obtained in 22% reaction yield) was 97% S-enantiomer and 2% R-enantiomer of α-[(Acetylthio)methyl]benzenepropanoic acid (enantiomeric excess=95%).

EXAMPLE 9

Same as example 6, except, *Geotrichum candidum* lipase from Amano Co. was used as the enzyme source. After 160 hours, the conversion was 64% based on the racemic material initially present. The enenatiomeric composition of the remaining unreacted substrate (obtained in 36% reaction yield) was 92% S-enantiomer and 8% R-enantiomer of α-[(Acetylthio)methyl]benzenepropanoic acid (enantiomeric excess=81%).

EXAMPLE 10

Same as example 6, except, Pseudomonas lipase AK from Amano Co. was used as the enzyme source. After 40 hours, the conversion was 60% based on the racemic material initially present. The enantiomeric composition of the remaining unreacted substrate (obtained in 40% reaction yield) was 97% S-enantiomer and 2% R-enantiomer of α-[(Acetylthio)methyl]benzenepropanoic acid (enantiomeric excess=95%).

EXAMPLE 11

10.0 g of lipase from *Pseudomonas fluorescens* (Amano lipase P-30) was added to 50 mL deionized water and the mixture centrifuged for 10 minutes at 1,000×G. A 40 mL portion of the supernatant was diluted to 200 mL with deionized water and to this enzyme solution was added 40 g of Celite Hyflo Supercel (commercially available diatomaceous earth). The mixture was incubated for 3 hours at 28° C. with gentle stirring. The enzyme was then precipitated onto the Hyflo Supercel by slowly adding 300 mL of ice-cold acetone to the mixture while stirring The mixture was filtered on a sintered glass vacuum filter and the filter cake washed with 300 mL ice-cold acetone The preparation was dried in a vacuum evaporator at 50° C. for 18 hours to yield an immobilized enzyme preparation with a water content of 0.45% w/w (Karl Fischer moisture analysis).

A 2 g portion of the above immobilized enzyme preparation was added to a solution of racemic α-[(Acetylthio)methyl]benzenepropanoic acid (405 mg) in 25 toluene. To this mixture, 60 mg of deionized water was added and the reaction mixture shaken on a gyrotary shaker at 280 rpm at 30° C. The degree of conversion was followed by gas chromatography of reaction mixture filtrates. After 16 hours, the conversion was 58% based on the racemic substrate initially present. The enantiomeric composition of the remaining unreacted substrate (obtained in 42% reaction yield) was 97.1% S-enantiomer and 2.9% R-enantiomer of α-[(Acetylthio)methyl]benzenepropanoic acid (enantiomeric excess=94.2%) as determined by chiral HPLC.

EXAMPLE 12

Immobilization of Enzyme and Use of Immobilized Enzyme

Three different carriers—XAD-7 (Amberlite XAD-7 nonionic polymeric absorbent, 20-60 mesh polyacrylate resin) XAD-2 (Amberlite XAD-nonionic polymeric absorbent, 20-60 mesh polystyrene resin) and Accurel PP (polypropylene resin 200-400 microns)—were used for immobilization procedures.

Crude Amano PS 30 lipase (10 g) was dissolved in 25 mL of distilled water and centrifuged at 10,000 rpm for 10 minutes to obtain clear supernatant. The carrier (1.3 g) in a 25-mL vial was washed 5 times with methanol and added to enzyme solution in a flask and gently agitated on a gyrotary shaker at room temperature. Adsorption of enzyme to the carrier was checked periodically by lipase assay (Sigma olive oil emulsion as substrate) and by protein remaining in filtrate. About 68%, 71% and 98% adsorption efficiency were obtained using XAD-7, XAD-2, and Accurel resins, respectively. After complete immobilization (20 to 24 hours), the carrier-enzyme slurry was filtered through a Millipore filter and the carrier was washed with about 300 mL of distilled water. Subsequently, the carrier containing the immobilized lipase was dried in a vacuum oven at room temperature.

Immobilized enzyme was evaluated for the enzymatic hydrolytic reactions as described in Example 6. The substrate was racemic α-[(Acetylthio)methyl]benzenepropanoic acid and the product was S-α-[(Acetylthio)methyl]benzenepropanoic acid. Reaction mixture in 10 mL of toluene contained 250 mg of substrate, 100 mg of immobilized lipase P-30 on Accurel polypropylene, and 0.1% water. Reaction was conducted at 28° C., 200 rpm. Enzyme was reused at least three times without any loss of activity or productivity (Table 1). Similar results were obtained with enzyme, immobilized on XAD-2 or XAD-7, used as the catalyst.

TABLE I

| Cycle # | Reaction Time (Hours) | Conversion (%) | Reaction Yield (%) | Optical Purity (%) | Enantiomeric Excess (e.c) |
|---|---|---|---|---|---|
| 1 | 21 | 57.7 | 42.3 | 98 | 96 |
| 2 | 27 | 64 | 36 | 99 | 98 |
| 3 | 21 | 58 | 42 | 97 | 94 |

EXAMPLE 13

Same as example 6, except *Aspergillus niger* lipase from Amano was used and the reaction mixture contained 160 mL of methanol.

The reaction mixture contained 250 mg of α-[(Acetylthio)methyl]benzenepropanoic acid in 10 mL of toluene with 1 gram of *Aspergillus* niger lipase, 0.1% (v/v) water and 160 mL methanol. The product was S-α-[(Acetylthio)methyl]benzenepropanoic acid. In this case both esterification of the carboxyl group and hydrolysis of the thioester occurred as follows:

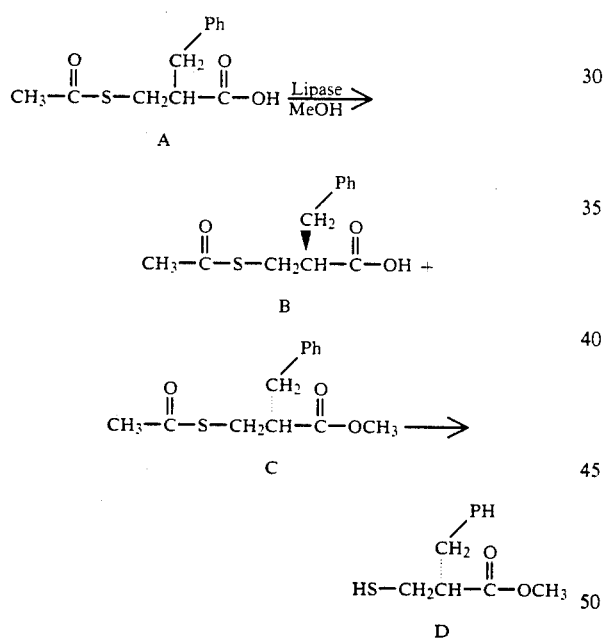

Reaction was monitored by gas chromatography. Compound A and B had retention times of 8.26 minutes, compound C had a retention time of 7.25 minutes and compound D had a retention time of 4.98 minutes. After 48 hours, the conversion was 79% based on the racemic material initially present. The enantiomeric composition of the remaining unreacted substrate (obtained in 21% reaction yield) was 95% S-enantiomer and 5% R-enantiomer of α-[(Acetylthio)methyl]benzenepropanoic acid (enantiomeric excess=90%).

EXAMPLE 14

Same as example 13, except, Novo Lipolase was used as the enzyme source. After 40 hours, the conversion was 80% based on the racemic material initially present. The enantiomeric composition of the remaining unreacted substrate (obtained in 20% reaction yield) was 88% S-enantiomer and 12% R-enantiomer of α-[(Acetylthio)methyl]benzenepropanoic acid (enantiomeric excess=76%).

What is claimed is:

1. A process for the preparation of a compound of the formula

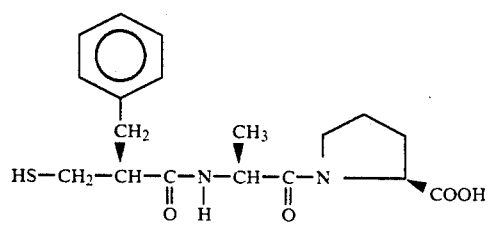

which comprises

A) coupling Boc alanine with a proline benzyl ester hydrochloride salt to form a Boc protected alanine proline benzyl ester having the formula

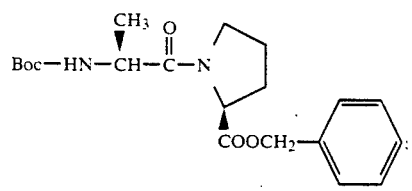

B) reacting the product of step A with trifluoroacetic acid and tosic acid to produce an alaproline benzyl ester tosic acid of formula

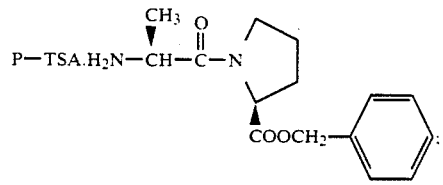

C) preparing a resolved carboxylic acid of the formula

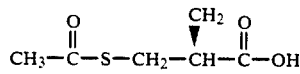

by treating a compound of formula

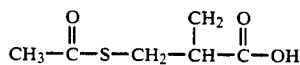

with an enzyme of microorganism containing an enzyme, capable of asymmetrically hydrolyzing the thioester bond in the presence of a solvent;

D) alkylating the resolved carboxylic acid with the alaproline benzyl ester tosic acid of step B to form a compound of formula

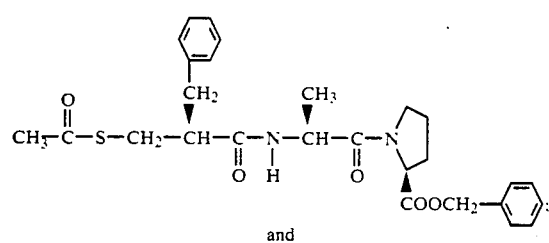
and
E) saponifying the above compound to provide the desired product.
* * * * *
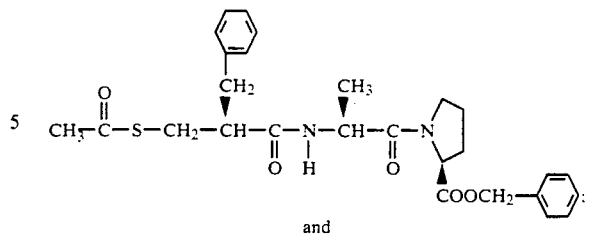
and
E) saponifying the above compound to provide the desired product.
* * * * *

UNITED STATES PATENT AND TRADEMARK OFFICE
CERTIFICATE OF CORRECTION

PATENT NO. : 5,177,006

DATED : January 5, 1993

INVENTOR(S) : Jeffrey M. Howell et al.

It is certified that error appears in the above-identified patent and that said Letters Patent is hereby corrected as shown below:

Column 16, lines 1 to 12 should be deleted.

Signed and Sealed this

Sixteenth Day of November, 1993

Attest:

BRUCE LEHMAN

*Attesting Officer*       *Commissioner of Patents and Trademarks*